United States Patent [19]

Rapaport

[11] Patent Number: 4,880,918

[45] Date of Patent: Nov. 14, 1989

[54] ARREST AND KILLING OF TUMOR CELLS BY ADENOSINE 5-DIPHOSPHATE AND ADENOSINE-5-TRIPHOSPHATE

[76] Inventor: Eliezer Rapaport, 1 Soldiers Field Park, Apt. 313, Boston, Mass. 02163

[21] Appl. No.: 397,897

[22] Filed: Jul. 13, 1982

[51] Int. Cl.[4] .................. C07H 19/16; A61K 31/70
[52] U.S. Cl. .................................................. 536/27
[58] Field of Search ................... 424/180; 536/27; 514/47

[56] References Cited

U.S. PATENT DOCUMENTS 4,396,609  8/1983  Daum et al. ................. 424/180

FOREIGN PATENT DOCUMENTS 0034697  4/1981  Japan ........................ 536/27

OTHER PUBLICATIONS

Chemical Abstracts, 98:119267f, (1983).
Chemical Abstracts, 91:15297e, (1979).
Chemical Abstracts, 99(19):156206b, (1983).
Chemical Abstracts, 97(25):214032p.
Rapaport et al., Cancer Research, 43,4402–4406, Sep., 1983.
Elmaleh et al., Proc. Natl. Acad. Sci. U.S.A., vol. 81, pp. 918–921, Feb., 1984.

Primary Examiner—John W. Rollins
Attorney, Agent, or Firm—Antonelli, Terry & Wands

[57] ABSTRACT

A process by which the growth of malignant cells, e.g., human malignant cells, in a host is arrested and killed by treatment of the cells with low doses of adenosine 5'-diphosphate (ADP) or adenosine 5'-triphosphate (ATP), while normal cells thereof are substantially unaffected, is disclosed. ADP and ATP are capable of permeating through the plasma membrane of a variety of tumor cells, e.g., human tumor cells, and are incorporated into the cellular acid-soluble nucleotide pools of these cells, without prior breakdown to adenosine 5'-monophosphate (AMP) or adenosine, resulting in inhibition of DNA synthesis and cellular growth followed by cell death, while normal animal cells do not allow penetration of ADP or ATP through their plasma membrane without prior degradation.

32 Claims, 5 Drawing Sheets

ARREST AND KILLING OF TUMOR CELLS BY ADENOSINE 5-DIPHOSPHATE AND ADENOSINE-5-TRIPHOSPHATE

BACKGROUND OF THE INVENTION

This invention relates to the use of adenosine 5'-diphosphate (ADP) and/or adenosine 5'-triphosphate (ATP) for selective inhibition of growth and subsequent killing of malignant cells, e.g., human malignant cells, thereby utilizing a normal metabolite for inhibiting, e.g., human tumor cell growth.

It is known to use antimetabolites (e.g., cytotoxic nucleosides or bases) such as purines and pyrimidines as antineoplastic drugs. However, such antimetabolites are taken up by both normal and tumor cells, and therefore not only can inhibit the growth of tumor cells, but also growth of normal cells.

U.S. Pat. No. 4,291,024 to Turcotte discloses a process for the preparation of liponucleotide analogs of nucleosides or bases having known cytotoxic activity (e.g., 1-$\beta$-D-arabinofuranosyl-cytosine, known as Ara-C). This patent discloses that these liponucleotide analogs of nucleosides provide a means for delivering cytotoxic nucleosides into the tumor cells. Once inside the cells, the cytotoxic nucleoside can be released in a phosphorylated form, thus circumventing the dependency upon kinase activity on the nucleoside itself. This is beneficial since the cytotoxic nucleosides or bases exert their anti-proliferative activities via the nucleoside triphosphate form. The objects stated in U.S. Pat. No. 4,291,024 do not mention delivery of normal cellular metabolites (e.g., ADP or ATP) into tumor cells via the liponucleotide analog; however, the liponucleotide analog of ADP falls within the broad disclosure of this U.S. patent. In any event, the liponucleotide analog disclosed by Turcotte enter the cancer cell via the process of lysosomo-tropism or related membrane phenomena; as such, these analogs can also enter normal non-cancerous cells (e.g., bone marrow, lymph node or intestinal epithelium cells), resulting in disruption of the normal cycling cell metabolism.

ATP is a known vasodilator that may cause circulatory changes in humans and experimental animals. See, e.g., Davies, et al., "Circulatory and Respiratory Effects of Adenosine Triphosphate in Man", in Circulation 3:543–550 (April 1951); Duff, et al., "A Quantitative Study of the Response to Adenosine Triphosphate of the Blood Vessels of the Human Hand and Forearm, in J. Physiol. 125:581–589 (1954); Rowe, et al., "The Systemic and Coronary Hemodynamic Effects of Adenosine Triphosphate and Adenosine", in American Heart J. 64:228–234 (1962). Moreover, cellular pools of acid-soluble nucleotides, especially ADP and ATP, have been previously shown by Rapaport and collaborators to act in the regulation of DNA replication and growth of mammalian cells. See, e.g., Rapaport, et al., "Incorporation of Adenosine into ATP:Formation of Compartmentalized ATP", in *Proc. Natl. Acad. Sci. USA*, Vol. 73, No. 9:3122–3125 (September 1976); Rapaport, et al., "Increased Incorporation of Adenosine into Adenine Nucleotide Pools in Serum-Deprived Mammalian Cells", in *Proc. Natl. Acad. Sci. USA*, Vol. 75, No. 3:1145–1147 (March 1978); Rapaport, et al., "Elevated Nuclear ATP Pools and ATP/ADP Ratios Mediate Adenosine Toxicity in Fibroblasts", *In Regulation of Macromolecular Synthesis by Low Molecular Weight Mediators*, Acadamic Press, 1979, pp. 223–231; Rapaport, et al., "Regulation of DNA Replication in S Phase Nuclei by ATP and ADP Pools", in *Proc. Natl. Acad. Sci. USA*, Vol. 76, No. 4:1643–1647 (April 1979); Rapaport, et al., "Selective High Metabolic Lability of Uridine, Guanosine and Cytosine Triphosphate in Response to Glucose Deprivation and Refeeding of Untransformed and Polyoma Virus-transformed Hamster Fibroblasts", in *J. Cell. Physiol.*, Vol. 101, No. 2:229–236 (November 1979); Rapaport, et al., "Selective High Metabolic Lability of Uridine Triphosphate in Response to Glucosamine Feeding of Untransformed and Polyoma Virus-transformed Hamster Fibroblasts", in *J. Cell. Physiol.*, 104:253–259 (1980); Rapaport, "Compartmentalized ATP Pools Produced from Adenosine Are Nuclear Pools", in *J. Cell. Physiol.*, 105:267–274 (1980); and Rapaport, et al., "Retinoic Acid-Promoted Expansion of Tofal Cellular ATP Pools in 3T3 Cells Can Mediate its Stimulatory and Growth Inhibitory Effects" in *J. Cell. Physiol.*, 110:318–322 (1982).

However, these references showing use of ADP and ATP as regulators of DNA replication and growth of mammalian cells do not disclose that the materials, or a process of using such materials, selectively attack malignant cells, e.g., human malignant cells, and not attack normal cells, leading to the arrest of growth and killing of said malignant cells while causing sustantially no arrest of growth or killing of normal cells.

SUMMARY OF THE INVENTION

Accordingly, it is an object of this invention to provide a process for selectively arresting and killing malignant cells, e.g., human malignant cells, while causing substantially no arrest or killing of normal cells.

It is a further object of this invention to provide a process for inhibiting tumor cell growth utilizing normal metabolites having selective penetration exclusively into tumor cells to disrupt cellular metabolism.

In order to accomplish the foregoing objects, applicant has found that exposure of a variety of malignant cells, e.g., a variety of types of human malignant cells, to low doses of ADP and/or ATP will result in marked inhibition of DNA synthesis and arrest of significant populations of cells in the S phase of their cycle, and continued exposure to such low doses of ADP and/or ATP will result in death of such malignant cells, with such effect on malignant cells occurring with substantially no effect on normal cells.

DETAILED DESCRIPTION OF THE INVENTION

Figure 1A:
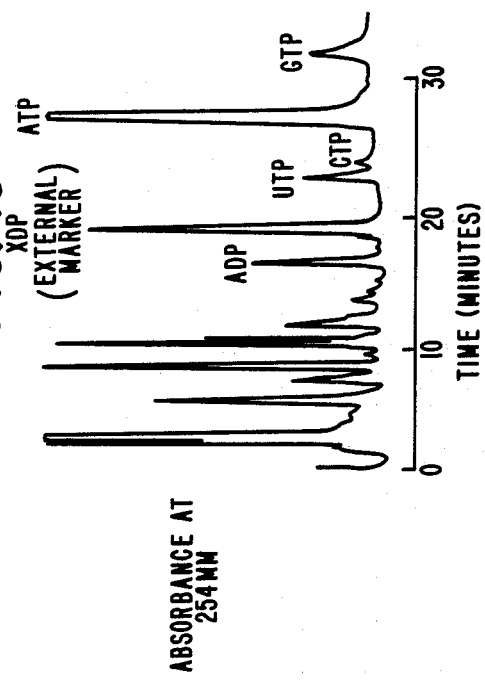
FIGS. 1A–1D are quantitative showings of the total cellular acid-soluble nucleotide pools for cell line designations HT29 and HS294T each treated with adenosine 5'-monophosphate (AMP) and ATP.

Applicant has found that ADP and ATP can permeate through the plasma membrane of tumor cells, e.g., human tumor cells, without prior degradation to adenosine -5'-monophosphate (AMP) or adenosine, with incorporation into cellular acid-soluble nucleotide pools followed by the disruption of cellular functions. Tumor cells from a variety of sources allow the direct incorporation of externally added ADP and/or ATP into their cellular acid-soluble nucleotide pools.

Such permeation by ADP or ATP through the plasma membrane of tumor cells without prior degradation to AMP or adenosine does not occur in normal animal cells; it is widely known that acid-soluble nucleotides are incapable of entering normal animal cells in intact form due to their negative charge, but must first be degraded to AMP and adenosine. The ability of ADP and/or ATP to permeate the plasma membrane of a variety of tumor cells, and not normal cells, is related to lesions in the plasma membrane found exclusively in many types of tumor cells.

By having the ADP and/or ATP incorporated into the cellular acid-soluble nucleotide pools of the tumor cells, such pools are altered, leading to the arrest of growth in the S phase of the cell cycle and eventual cell death. These effects are specific to ADP and ATP and cannot be achieved by treatment with other adenine nucleotides or adenosine. Thus, exposure of a variety of human tumor cells to, e.g., 40 µM of ADP and/or ATP for 48 hours results in marked inhibition of DNA synthesis and arrest of significant populations of cells in the S phase of their cycle. Continued treatment of such tumor cells with, e.g., 40 µM of ADP or ATP beyond 48 hours results in significant amounts of cell death. The exposure of human tumor cells to ADP or ATP for the purpose of arresting these cells in the S phase of their cycle need not be continuous. Cellular death however, is directly related to the magnitude of S phase arrest that has been achieved during the 48 hours after the onset of treatment. Thus, the criterion for obtaining human tumor cell death by this procedure is the initial production of S phase arrest in these cells.

Since ADP and/or ATP in a pharmaceutically acceptable salt form are very soluble in aqueous solutions, they provide very suitable means for administration as anticancer agents in humans. Sustaining sufficient blood levels of ADP and/or ATP can thus be achieved by injections or infusions. Phosphomonoesterase activity which is especially high in the kidney would tend to metabolize ADP and/or ATP and lower their blood plasma levels. It has, however, been reported that phosphomonoesterase activities of human tissues are low in comparison with mice and other experimental animals with especially low phosphomonoesterase levels reported for human kidneys. Whereas the use of derivatives of anticancer nucleotides, nucleosides or bases do not differentiate between, and are cytotoxic to tumor cells as well as to normally proliferating cells in the host (e.g., bone marrow, lymph node and intestinal epithelium cells), the use of low doses (25-100 µM) of ADP and/or ATP affords a desired antineoplastic selectivity. A more preferable range for the ADP or ATP dosage is 40-80 µM. Only much higher doses of ATP (above 250 µM) were reported to affect cellular components of the immune system and it is demonstrated in this disclosure that human intestinal cells are not affected by low doses of either ADP or ATP.

The ADP and/or ATP can be employed in a pharmaceutically acceptable salt form and can be employed in a variety of conventional pharmaceutical preparations. These preparations can contain organic or inorganic material suitable for internal administration. The high solubility of ADP and/or ATP salts in isotonic aqueous solutions of sodium chloride, etc., enable administration of these agents in the form of injection or infusion of single or multiple doses. The injection or infusion can be intravenous or intra-arterial. ADP and/or ATP are also suitable for oral, enteral or topical application when employed with conventional organic or inorganic carrier substances. The effective doses should be in the range of 1-100 mg/kg of body weight for oral or topical administration and 0.05-20 mg/kg of body weight for injections. Intravenous or intra-arterial infusions of ADP and/or ATP, in a suitable salt form, is preferably administered at a rate of 0.01-1.5 mg/kg of body weight per minute.

For solid tumors, infusion of ADP or ATP is the preferable administration method, since it can deliver greater amounts of ADP or ATP into the vicinity of the tumor with minimal physiological effects on the blood flow.

With regard to the rate of infusion of the ADP and/or ATP, the various references, cited previously, disclosing that ATP is a known vasodilator, are noted. From these references, it can be appreciated that single rapid injections of 40 mg of the sodium salt of ATP, either intravenously or intra-arterially, produced small subjective and physiological changes in human subjects. Slow injections or infusions of the same dose of ATP produced much lesser or no response at all (see Davies, et al., supra.)

Experiments on dogs have shown that the threshhold dose which would elicit any kind of an effect on the coronary circulation is 2 micromole (1.2 mg) of ATP per kg weight per minute (see Rowe, et al., supra.) Infusions in these experiments lasted for 30 minutes. It has also been established that vasodilation by ATP was more profound if the magnesium salt of ATP was used instead of its sodium salt. No subjective sensation or any physiological effects were observed upon infusions of 1 mg/minute of sodium salt of ATP into the brachial artery of healthy subjects (see Duff, et al., supra.)

A variety of human tumor cell lines and a cell line derived from human intestine cells (i.e., normal cells) are utilized (summarized in Table 1) for demonstration of the invention in a nonlimiting fashion.

TABLE 1

Cells of Human Origin Used to Demonstrate the Invention

| Cell Line Designation | Tissue of Origin | Source of the Cells | Cell Morphology | Growth Medium |
|---|---|---|---|---|
| CAPAN-1 | Pancreatic tumor | Sloan-Kettering Inst. | Epitheloid | RPMI 1640 |
| BxPc | Pancreatic tumor | Boston University School of Medicine | Epitheloid | RPMI 1640 |
| HT29 | Cancer of the colon | Naval Bioscience Labs | Epitheloid | MEM |
| HS294T | Melanoma metastatic to lymph node | Naval Bioscience Labs | Epitheloid | MEM |
| HS584T | Mammary gland tumor | Naval Bioscience Labs | Fibroblastic | RPMI 1640 |
| HS586INT | Normal intestine | Naval Bioscience Labs | Fibroblastic | RPMI 1640 |

Media: RPMI 1640 - RPMI medium 1640, Grand Island Biological Co., Cat. No. H-18. MEM - Eagle's minimal essential medium with non-essential amino acids, Grand Island Biological Co., Cat. No. F-15.

Cells are cultured in 100-mm or 35-mm plastic petri dishes, as discussed below, at 37° C. in a humidified atmosphere of 90% air, 10% $CO_2$ and in media supplemented with 10% fetal calf serum. The use of heat inactivated (20 hours at 58° C.) fetal calf serum is important since untreated serum contains high phosphomonoesterase and phosphodiesterase activities which lead to rapid degradation of adenine nucleotides. Cells are passaged every 4–5 days. All cells have been demonstrated to be free of Mycoplasma contamination.

Effects of Low Doses of Adenine Nucleotides on DNA Synthesis and Total Cellular Acid-soluble Nucleotide Pools Actively proliferating cells (logarithmic phase) in 35-mm petri dishes are exposed to a variety of nucleotides in 2 ml of the corresponding media supplemented with 10% heat inactivated fetal calf serum (20 hours at 58° C.). After 48 hours the medium is removed and the cells are exposed to [$^3$H] thymidine in 1 ml of the corresponding media without serum (1 $\mu$Ci/ml of medium) for 1 hour; the medium is removed and the cells treated immediately with 1 ml of ice-cold 15% trichloroacetic acid (TCA) containing 3.4 nmol of xanthosine diphosphate (XDP, quantitative marker for determination of acid soluble nucleotide pools by high pressure liquid chromatography). Extraction of acid-soluble nucleotides is performed on ice for 30 minutes. The TCA extract is neutralized by vigorous extraction with 0.5 M tri-n-octylamine in Freon-113. The neutralized extract is used for HPLC analysis (on a Waters Associates ALC 204 instrument) of acid-soluble nucleotides on strong ion exchange columns (Whatman's Partisil-10 SAX).

Figure 1C:
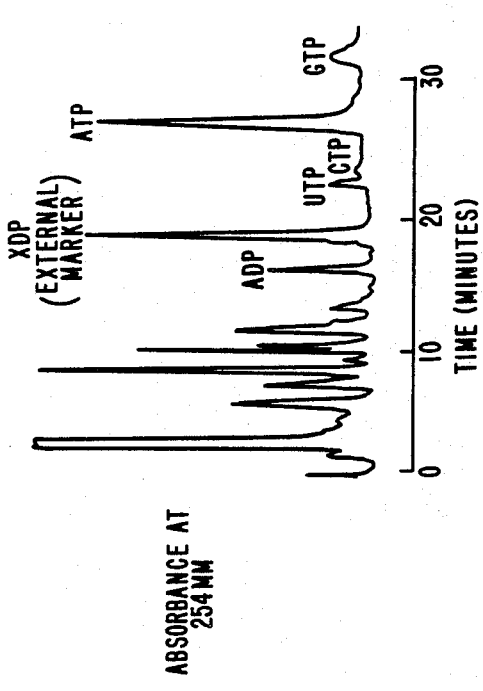
Figure 1B:
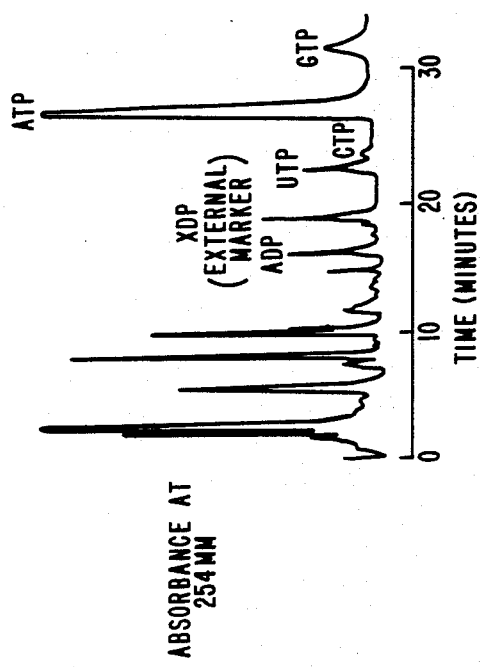
Figure 1D:
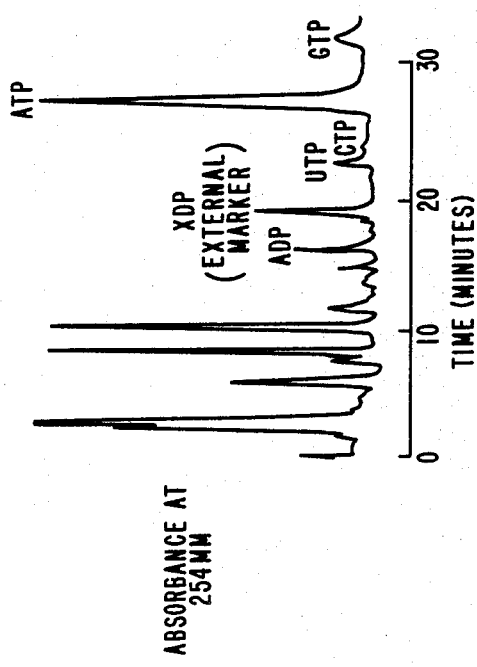

Chromatographic separation of total cellular acid-soluble nucleotides is demonstrated for HT29 and HS294T cells after 48 hours treatment with either AMP or ATP in FIGS. 1A–1D. In FIGS. 1A–1D, the HT29 cells treated for 48 hours with AMP and ATP are shown in A and B, respectively, and the HS294T cells treated for 48 hours with AMP and ATP are shown in FIGS. 1C and 1D, respectively. The extracts used in producing FIGS. 1A–1D were prepared from FIG. 1A:$1.4 \times 10^6$; FIG. 1B:$0.8 \times 10^6$; FIG. 1C:$0.3 \times 10^6$; and FIG. 1D:$0.2 \times 10^6$ cells, and treatment was with 40 $\mu$M of the nucleotide. Peaks are integrated electronically with a Hewlett-Packard HP3380A integrator. Specific radioactivity of the [$^3$H]dTTP peak is determined by collection of all the dTTP peak. The TCA insoluble material after incorporation of [$^3$H]thymidine is washed twice with ice-cold 5% TCA and twice with 95% ethanol. The acid-insoluble material is then lysed in 1 ml of 0.3 M NaOH and counted. Tables 2 through 6 demonstrate the effects on DNA synthesis and total cellular acid-soluble nucleotide pools of 48 hours treatment of a variety of human tumor cells with low doses of adenosine, AMP, ADP and ATP.

Tables 2 to 6.

Figure 3:
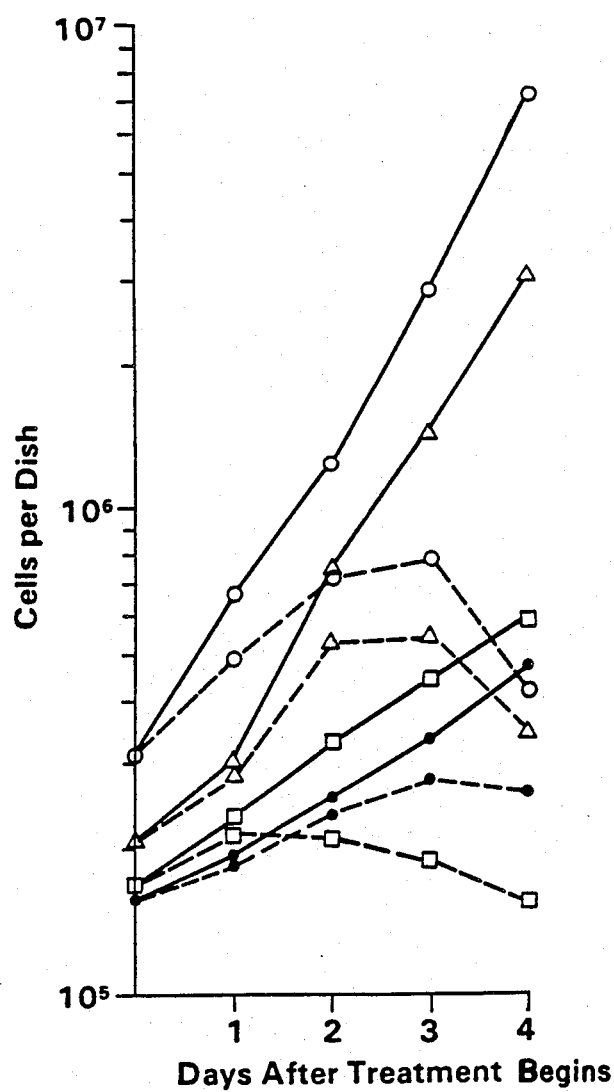
FIG. 3 shows the growth curves of several types of human tumor cells, either untreated or treated with 40 $\mu$M of ADP.

Demonstration of the effects of 40 $\mu$m of adenosine, AMP, ADP or ATP treatment for 48 hours on DNA synthesis and acid-soluble nucleotide pools of human tumor cells. In each table, the initial cell numbers are identical in control cells (no treatment) and cells treated with a variety of adenine nucleotides. The corresponding cell growth curves are illustrated in FIG. 3.

TABLE 2

CAPAN-1 Cells

| Nucleotide | Final Cell Number | ADP | ATP | UTP | GTP | [$^3$H]dTTP cpm | Acid-Insoluble cpm | DNA Synthesis/ % of Control |
|---|---|---|---|---|---|---|---|---|
| | | | nmols/$10^6$ cells | | | | | |
| None | $7.0 \times 10^5$ | 1.3 ± 0.1 | 9.5 ± 0.4 | 3.1 ± 0.1 | 2.4 ± 0.2 | 4556 | 407252 | 100 |
| Adenosine | $7.1 \times 10^5$ | 1.3 ± 0.1 | 11.7 ± 0.3 | 2.6 ± 0.1 | 2.3 ± 0.1 | 4967 | 411156 | 93 |
| AMP | $7.0 \times 10^5$ | 1.1 ± 0.1 | 10.5 ± 0.1 | 2.7 ± 0.1 | 2.3 ± 0.2 | 5049 | 410276 | 90 |
| ADP | $5.5 \times 10^5$ | 0.9 ± 0.1 | 10.9 ± 0.3 | 0.9 ± 0.1 | 1.5 ± 0.1 | 7702 | 408509 | 59 |
| ATP | $5.2 \times 10^5$ | 1.0 ± 0.1 | 10.3 ± 0.2 | 0.8 ± 0.1 | 1.4 ± 0.1 | 8619 | 453678 | 59 |

TABLE 3.

BxPc Cells

| Nucleotide | Final Cell Number | ADP | ATP | UTP | GTP | [$^3$H]dTTP cpm | Acid-Insoluble cpm | DNA Synthesis % of Control |
|---|---|---|---|---|---|---|---|---|
| | | | nmols/$10^6$ cells | | | | | |
| None | $2.6 \times 10^5$ | 2.1 ± 0.1 | 16.0 ± 0.2 | 5.3 ± 0.2 | 4.9 ± 0.1 | 696 | 20247 | 100 |

TABLE 3.-continued

BxPc Cells

| Nucleotide | Final Cell Number | ADP | ATP | UTP | GTP | [³H]dTTP cpm | Acid-Insoluble cpm | DNA Synthesis % of Control |
|---|---|---|---|---|---|---|---|---|
| | | | nmols/10⁶ cells | | | | | |
| Adenosine | 2.6 × 10⁵ | 2.0 ± 0.1 | 15.7 ± 0.2 | 5.1 ± 0.3 | 4.5 ± 0.3 | 793 | 21657 | 94 |
| AMP | 2.6 × 10⁵ | 1.9 ± 0.1 | 16.4 ± 0.4 | 4.4 ± 0.2 | 4.1 ± 0.1 | 920 | 24391 | 91 |
| ADP | 2.5 × 10⁵ | 1.8 ± 0.1 | 15.7 ± 0.3 | 2.3 ± 0.1 | 3.2 ± 0.1 | 1727 | 34176 | 68 |
| ATP | 2.4 × 10⁵ | 2.0 ± 0.2 | 15.6 ± 0.3 | 2.3 ± 0.1 | 3.3 ± 0.2 | 1803 | 42241 | 80 |

TABLE 4

HS584T

| Nucleotide | Final Cell Number | ADP | ATP | UTP | GTP | [³H]dTTP cpm | Acid-Insoluble cpm | DNA Synthesis % of Control |
|---|---|---|---|---|---|---|---|---|
| | | | nmols/10⁶ cells | | | | | |
| None | 1.3 × 10⁵ | 3.9 ± 0.2 | 17.4 ± 0.2 | 6.2 ± 0.2 | 4.3 ± 0.2 | 7435 | 12189 | 100 |
| Adenosine | 1.3 × 10⁵ | 4.0 ± 0.2 | 18.7 ± 0.4 | 5.7 ± 0.2 | 3.5 ± 0.2 | 3019 | 5355 | 108 |
| AMP | 1.2 × 10⁵ | 3.2 ± 0.1 | 19.5 ± 0.9 | 5.9 ± 0.2 | 3.7 ± 0.3 | 2905 | 4817 | 101 |
| ADP | 1.1 × 10⁵ | 4.5 ± 0.2 | 18.7 ± 0.5 | 4.4 ± 0.1 | 3.1 ± 0.2 | 2761 | 2213 | 49 |
| ATP | 1.1 × 10⁵ | 3.9 ± 0.1 | 19.2 ± 0.5 | 4.5 ± 0.2 | 3.0 ± 0.2 | 2369 | 2302 | 59 |

TABLE 5

HT29

| Nucleotide | Final Cell Number | ADP | ATP | UTP | GTP | [³H]dTTP cpm | Acid-Insoluble cpm | DNA Synthesis % of Control |
|---|---|---|---|---|---|---|---|---|
| | | | nmols/10⁶ cells | | | | | |
| None | 1.4 × 10⁶ | 0.4 ± 0.1 | 5.1 ± 0.1 | 1.5 ± 0.1 | 1.0 ± 0.1 | 5746 | 158626 | 100 |
| Adenosine | 1.3 × 10⁶ | 0.5 ± 0.1 | 5.9 ± 0.1 | 1.2 ± 0.1 | 1.1 ± 0.2 | 6198 | 189502 | 110 |
| AMP | 1.3 × 10⁶ | 0.6 ± 0.1 | 6.1 ± 0.1 | 1.2 ± 0.1 | 1.1 ± 0.1 | 7087 | 201566 | 103 |
| ADP | 0.8 × 10⁶ | 1.0 ± 0.1 | 9.9 ± 0.2 | 0.9 ± 0.1 | 1.1 ± 0.1 | 12724 | 231614 | 65 |
| ATP | 0.9 × 10⁶ | 1.0 ± 0.1 | 9.7 ± 0.3 | 0.9 ± 0.1 | 1.3 ± 0.1 | 11646 | 274377 | 85 |

TABLE 6

HS294T

| Nucleotide | Final Cell Number | ADP | ATP | UTP | GTP | [³H]dTTP cpm | Acid-Insoluble cpm | DNA Synthesis % of Control |
|---|---|---|---|---|---|---|---|---|
| | | | nmols/10⁶ cells | | | | | |
| None | 0.33 × 10⁵ | 1.5 ± 0.1 | 9.9 ± 0.3 | 3.7 ± 0.1 | 3.1 ± 0.2 | 8079 | 57429 | 100 |
| Adenosine | 0.32 × 10⁵ | 1.6 ± 0.1 | 11.2 ± 0.3 | 3.1 ± 0.2 | 2.9 ± 0.2 | 9437 | 67177 | 100 |
| AMP | 0.30 × 10⁵ | 1.7 ± 0.1 | 11.1 ± 0.2 | 2.8 ± 0.2 | 2.7 ± 0.1 | 9388 | 72275 | 108 |
| ADP | 0.21 × 10⁵ | 2.2 ± 0.2 | 10.8 ± 0.2 | 1.5 ± 0.2 | 1.9 ± 0.1 | 6478 | 36419 | 79 |
| ATP | 0.21 × 10⁵ | 2.2 ± 0.1 | 11.3 ± 0.3 | 1.6 ± 0.2 | 2.1 ± 0.2 | 6755 | 33770 | 70 |

All determinations represent the mean of three experiments (± standard error).
Determination of cellular acid-soluble nucleotides is illustrated in FIG. 1.

The data outlined in Tables 2-6 yield the following conclusions:
1. Treatment of a variety of human tumor cells with low doses of ADP or ATP for as short a time as 48 hours produces inhibition of both DNA synthesis and cellular growth.
2. The effects on cellular growth is unique to ADP and ATP and cannot be duplicated by any of their degradation products, namely, adenosine and AMP.
3. The activity of ADP and ATP in inhibiting cellular growth is due to their direct incorporation into cellular acid-soluble nucleotide pools by penetrating the plasma membrane of a variety of human tumor cells. The incorporation of external ADP or ATP into cellular acid-soluble nucleotide pools causes a severe reduction in total cellular UTP pools and to a lesser extent a depletion of GTP pools. Only in one case (HT29) is there a substantial increase in cellular ATP pools after exposure of the cells to ADP or ATP.

Similar treatment of normal human intestine cells (HS586INT) does not produce any inhibition of DNA synthesis or cellular growth with minor differences in cellular acid-soluble nucleotide pools. The effects on cellular acid-soluble nucleotide pools of HS586INT produced by ADP or ATP treatment are similar to the effects produced by either AMP or adenosine treatment. It is thus concluded that in the case of HS586INT there is prior breakdown of ADP and ATP to AMP or adenosine, before incorporation into cellular acid-soluble nucleotide pools, without any effect on DNA synthesis or cellular growth.

Figure 2:
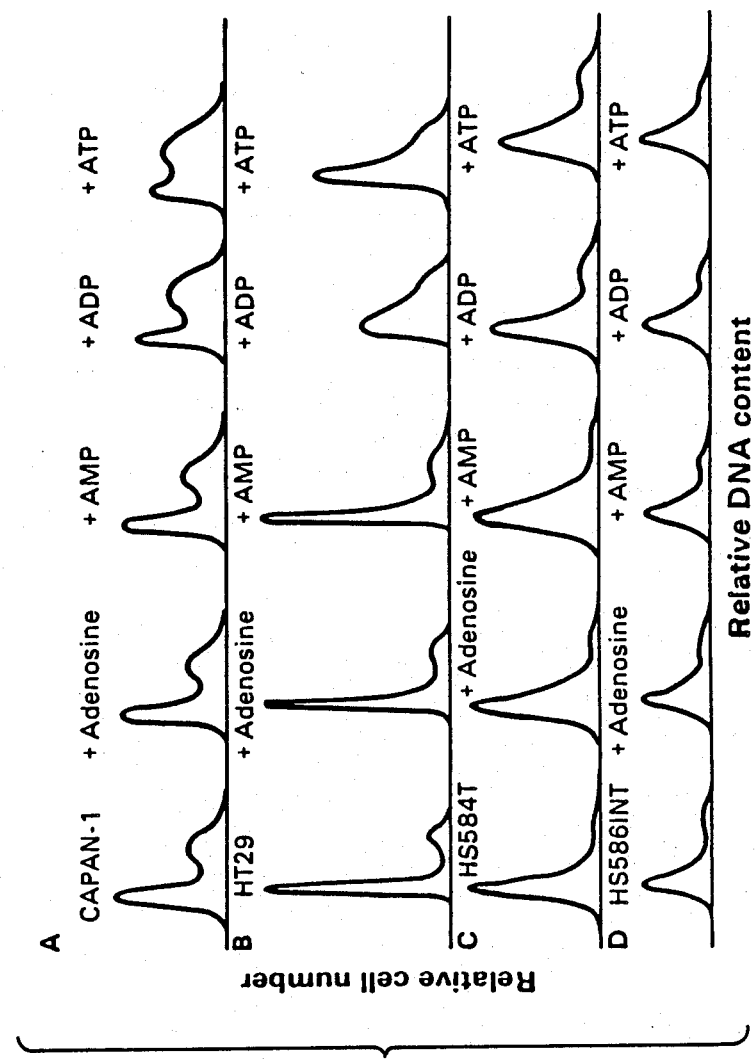
FIG. 2 shows the DNA distribution of human tumor cells (CAPAN-1, HT29, and HS584T) and normal human intestine cells (HS586INT) after 48 hours treatment with 40 $\mu$M of adenosine, AMP, ADP or ATP, comparisons being made with non-treated cells.

Flow Microfluorimetric Analyses Demonstrate That ADP and ATP Inhibit the Growth of Human Tumor Cells by Arresting the Cells in the S Phase of Their Cycle Cells are cultured in 100-mm petri dishes. Asynchronous cultures are treated with nucleotides in 10 ml of the corresponding media supplemented with heat inactivated fetal calf serum for 48 hours. The cells are then removed from the dish by trypsin/EDTA treatment. DNA fluorescent staining is achieved by treating 10⁶ cells with 0.3 ml of staining solution composed of 0.05 mg/ml propidium iodide in 0.1% sodium citrate and 0.1% Nonidet P-40. Stained cells are subjected to flow microfluorimetric analysis utilizing Ortho Diagnostic Systems Cytofluorograph System 50H with a 500 mWatts excitation at 488 nm. Total fluorescence was measured in the 590+ nm range. FIG. 2 illustrates the results for three of the human tumor cell lines and one normal human intestine cell line. Relative DNA content of cells indicate cell populations in $G_1$ phase (left peak), S phase (trough), and $G_2+M$ phase (right peak). Treatment of human tumor cells with low doses of ADP or ATP for 48 hours leads to substantial increases in S phase cells in all the cases of human tumor cells tested. Normal cell populations HS586INT do not show any change in their DNA distribution after similar treatment.

The conclusion based on the data presented in FIG. 2 is that human tumor cells are arrested by ADP and ATP treatment specifically in the S phase of their cycle. The arrest of growth is attributed directly to ADP or ATP treatment and not to their degradation products since neither AMP nor adenosine produce any noticeable effects on the DNA distribution of human tumor cells.

Treatment With Low Doses of ADP or ATP for Periods Longer Than 48 Hours is Lethal to Human Tumor Cells Human tumor cells were cultured in 35- mm petri dishes and treated with 2 ml of the corresponding media supplemented with 10% heat inactivated fetal calf serum and containing adenosine, AMP, ADP and ATP. Cell numbers were determined at different time periods after the start of treatment by removing the cells with trypsin/EDTA and counting them in an electronic particle counter (Coulter Electronics). Growth curves of human tumor cells with and without exposure to low doses of ADP are illustrated in FIG. 3. FIG. 3 demonstrates in a nonlimiting fashion that treatment of human tumor cells with ADP for periods of time longer than 48 hours results in cell death. In FIG. 3, (———) denotes untreated cells and (-----) denotes cells treated with 40 μM ADP. As for the specific types of cells, (O) denotes HT29 cells, (□) denotes HS294T cells, (Δ) denotes CAPAN-1 cells and ( ) denotes BxPc cells. Similar results are obtained for ATP treatment but not for treatment with adenosine or AMP. It can thus be seen that treatment of human tumor cells with ADP or ATP is lethal to these cells after the initial arrest of growth discussed in the previous section of this application. The killing of human tumor cells by ADP or ATP is not attributed to their degradation products adenosine or AMP, since these agents fail to produce similar results.

Figure 4A:
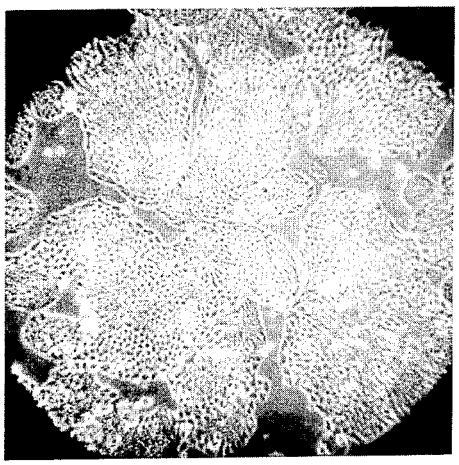
FIGS. 4A–4C are photomicrographs (x50) of HT29 cells——human colon adenocarcinoma——without treatment, with 4 days treatment according to the invention with 40 $\mu$M ADP, and with 4 days treatment according to the invention with 40 $\mu$M ATP, respectively.
Figure 4B:
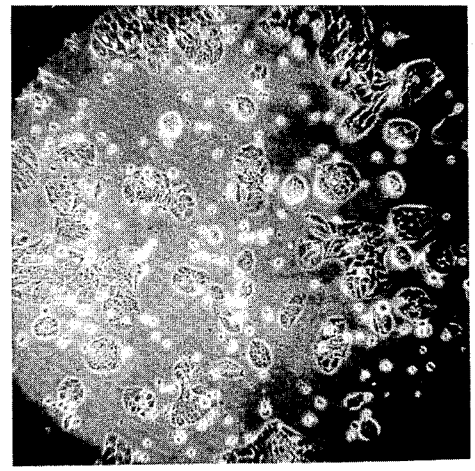
Figure 4C:
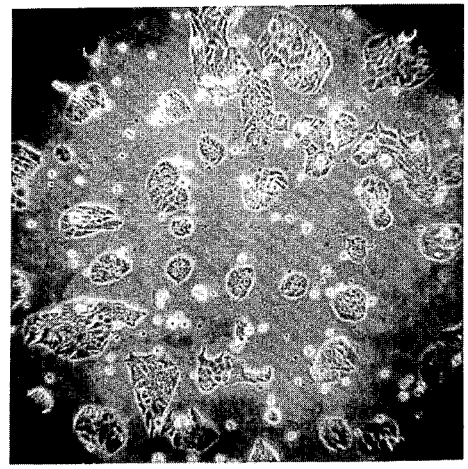
Figure 5A:
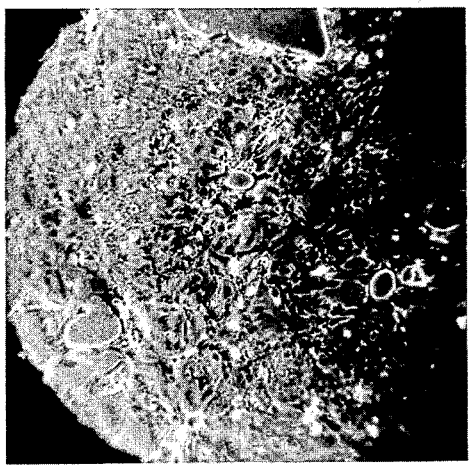
FIGS. 5A-5C are photomicrographs (x50) of CA-PAN-1 cells——human pancreatic adenocarcinoma——without treatment, with 4 days treatment according to the invention with 40 µM ADP, and with 4 days treatment according to the invention with 40 µM ATP, respectively.
Figure 5B:
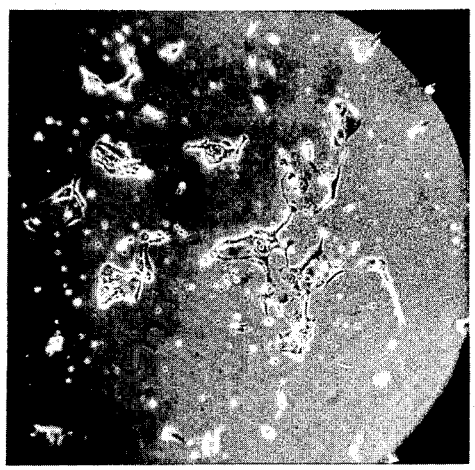
Figure 5C:
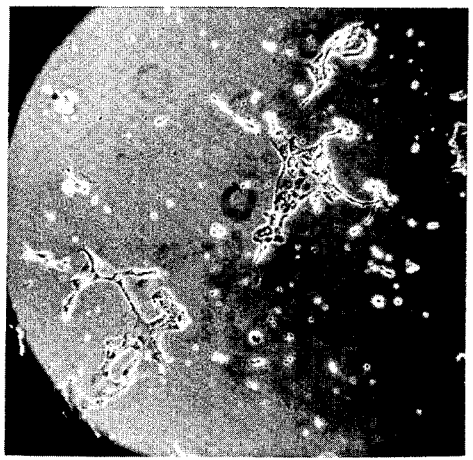

The lethal effects of low doses of ADP and ATP on two representative human tumors are demonstrated in the photomicrographs of FIGS. 4 and 5. As can be appreciated, the extent of the tumors after 4 days of treatment with either ADP (see FIGS. 4B and 5B) or ATP (see FIGS. 4C and 5C), according to this invention, is decreased as compared with the untreated tumors (see FIGS. 4A and 5A).

While I have shown and described several embodiments in accordance with the present invention, it is understood that the same is not limited thereto but is susceptible of numerous changes and modifications as known to one having ordinary skill in the art and I therefore do not wish to be limited to the details shown and described herein, but intend to cover all such modifications as are encompassed by the scope of the appended claims.

I claim:

1. A process for selectively entering and arresting the growth of tumor cells in a host while substantially not affecting normal cells thereof comprising the step of exposing said tumor cells to low doses of at least one of adenosine 5'-diphosphate and adenosine 5'-triphosphate, in a pharmaceutical preparation, said low doses being in an amount sufficient to inhibit DNA synthesis in said tumor cells while said normal cells are substantially unaffected.

2. A process according to claim 1, wherein said low doses are within the range of 25–100 μM.

3. A process according to claim 2, wherein said low doses are within the range of 40–80 μM.

4. A process according to claim 1 or 2, wherein said step of exposing continues for more than 48 hours, whereby significant numbers of said tumor cells are killed.

5. A process according to claim 4, wherein said tumor cells are human tumor cells.

6. A process according to claim 5, wherein said human tumor cells are a solid tumor.

7. A process according to claim 5, wherein said human tumor cells are selected from the group consisting of CAPAN-1, BxPc, HT29, HS294T and HS584T.

8. A process according to claim 1, wherein said step of exposing includes delivering said adenosine 5'-diphosphate, adenosine 5'-triphosphate or pharmaceutically acceptable salt thereof to the site of said tumor cells.

9. A process according to claim 8, wherein said delivering is accomplished by injection, infusion, oral administrating, enteral application or topical application.

10. A process according to claim 9, wherein said delivering is accomplished by oral administration or topical application, with a dosage of 1–100 mg/kg of body weight of said host.

11. A process according to claim 9, wherein said delivering is accomplished by injection, with a dosage of 0.05–20 mg/kg of body weight of said host.

12. A process according to claim 9, wherein said delivering is accomplished by infusion, at a rate of 0.01–1.5 mg/kg of body weight of said host per minute.

13. A process according to claim 1, wherein said at least one of adenosine 5'-diphosphate and adenosine 5'-triphosphate, in a pharmaceutical preparation, is a salt of adenosine 5'-diphosphate or adenosine 5'-triphosphate.

14. A process according to claim 13, wherein said salt is a complex salt.

15. A process for selectively entering and arresting the growth of tumor cells in the presence of normal cells, while substantially not affecting said normal cells, comprising the step of exposing said tumor cells in the presence of normal cells to low doses of adenosine 5'-diphosphate or adenosine 5'-triphosphate, in a pharmaceutical preparation, said low doses being in an amount sufficient to inhibit DNA synthesis in said tumor cells while said normal cells are substantially unaffected.

16. A process according to claim 15, wherein said step of exposing continues for more than 48 hours, whereby significant numbers of said tumor cells are killed.

17. A process according to claim 16, wherein said low doses are within the range of 25–100 μM.

18. A process according to claim 17, wherein said tumor cells are human tumor cells.

19. A process according to claim 18, wherein said adenosine 5'-diphosphate or adenosine 5'-triphosphate, in a pharmaceutical preparation, comprises adenosine 5'-diphosphate, adenosine 5'-triphosphate or pharmaceutically acceptable salts thereof.

20. A process according to claim 19, wherein said human tumor cells are a solid tumor.

21. A process according to claim 20, wherein said human tumor cells are selected from the group consisting of CAPAN-1, BxPc, HT29, HS294T and HS584T.

22. A process according to claim 1 or 15, wherein said tumor cells have a plasma membrane such that the adenosine 5'-diphosphate and adenosine 5'-triphosphate can selectively permeate therethrough while not permeating through the plasma membrane of normal cells, whereby the adenosine 5'-diphosphate and adenosine 5'-triphosphate, without prior degradation to adenosine 5'-monophosphate or adenosine, can selectively permeate through the plasma membranes of the tumor cells and not through the normal cells, whereby DNA synthesis in the tumor cells is inhibited while said normal cells are substantially not affected.

23. A process according to claim 22, wherein said doses are sufficient to arrest the growth of significant portions of said tumor cells in the S phase of their cycle.

24. A process according to claim 22, wherein said tumor cells are malignant tumor cells.

25. A process according to claim 1, wherein said at least one of adenosine 5'-diphosphate and adenosine 5'-triphosphate, in a pharmaceutical preparation, includes organic or inorganic materials suitable for internal administration into the host, in addition to at least one of adenosine 5'-diphosphate, adenosine 5'-triphosphate, and pharmaceutically acceptable salt forms thereof.

26. A process according to claim 1 or 15, wherein said doses are sufficient to arrest the growth of significant portions of said tumor cells in the S phase of their cycle.

27. A process according to claim 1, 2, 15 or 17, wherein said tumor cells have lesions in the plasma membrane permitting permeation of adenosine 5'-diphosphate or adenosine 5'-triphosphate therethrough without prior degradation thereof to adenosine 5'-monophosphate or adenosine.

28. A process for selectively permeating adenosine 5'-diphosphate or adenosine 5'-triphosphate into tumor cells in the presence of normal cells, without prior degradation of the adenosine 5'-diphosphate or adenosine 5'-triphosphate and without permeation of adenosine 5'-diphosphate or adenosine 5'-triphosphate into said normal cells, comprising the step of exposing said tumor cells in the presence of normal cells to low doses of at least one of adenosine 5'-diphosphate and adenosine 5'-triphosphate, in a pharmaceutical preparation, said low doses being within the range of 25–100 $\mu$M.

29. A process according to claim 28, wherein said tumor cells are selected from the group consisting of CAPAN-1, BxPc, HT29, HS294T and Hs584T.

30. A process according to claim 29, wherein said tumor cells are in a host.

31. A process according to claim 28, wherein said tumor cells have lesions in the plasma membrane permitting permeation of adenosine 5'-diphosphate or adenosine 5'-triphosphate therethrough without prior degradation thereof to adenosine 5'-monophosphate or adenosine.

32. A process according to claim 1, 15 or 28, wherein said tumor cells are malignant tumor cells.

* * * * *